United States Patent [19]
McFall et al.

[11] Patent Number: 6,001,306
[45] Date of Patent: Dec. 14, 1999

[54] INTEGRATED OXYGENATOR AND HEAT EXCHANGER

[75] Inventors: Frank B. McFall, Haverhill; Bulent Sert, Marblehead; Kenneth E. Buckler, Methuen, all of Mass.; Alfred P. Intoccia, Eden Prairie, Minn.; Martin J. Weinstein, Charlotte, N.C.; Ven Ramen, Framingham, Mass.

[73] Assignee: C. R. Bard, Inc., Murray Hill, N.J.

[21] Appl. No.: 08/744,869

[22] Filed: Nov. 7, 1996

[51] Int. Cl.⁶ ................................................ A61M 1/14
[52] U.S. Cl. .............................. 422/46; 422/45; 422/48
[58] Field of Search ................... 422/45, 46, 48; 210/175; 165/164, 165

[56] References Cited

U.S. PATENT DOCUMENTS

| | | | |
|---|---|---|---|
| 2,905,447 | 9/1959 | Huet et al. .............................. | 165/165 |
| 2,934,067 | 4/1960 | Calvin ...................................... | 422/46 |
| 3,807,958 | 4/1974 | Brumfield ................................ | 422/46 |
| 3,898,045 | 8/1975 | Bowley .................................... | 422/46 |
| 4,058,369 | 11/1977 | Bentley et al. .......................... | 422/47 |
| 4,073,622 | 2/1978 | Luppi ....................................... | 422/47 |
| 4,151,088 | 4/1979 | Wolf, Jr. et al. ....................... | 210/180 |
| 4,179,364 | 12/1979 | Bratten et al. ...................... | 210/321.77 |
| 4,228,125 | 10/1980 | Lobdell et al. ......................... | 422/46 |
| 4,261,951 | 4/1981 | Milev ....................................... | 422/46 |
| 4,451,562 | 5/1984 | Elgas et al. .............................. | 435/2 |
| 4,490,331 | 12/1984 | Steg, Jr. ................................... | 422/46 |
| 4,818,490 | 4/1989 | Carson et al. ........................... | 422/46 |
| 4,902,476 | 2/1990 | Gordon et al. .......................... | 422/46 |
| 5,225,161 | 7/1993 | Mathewson et al. ................... | 422/46 |
| 5,270,004 | 12/1993 | Cosentino et al. ..................... | 422/46 |
| 5,358,689 | 10/1994 | Jones et al. .............................. | 422/46 |

OTHER PUBLICATIONS

Nishimura et al. ("Flow Characteristics in a Channel with Symmetric Wavy Wall for Steady FLow", J. Chem. Eng. Jpn. 1984, 17(50, 466–71), 1984.

*Primary Examiner*—Robert Warden
*Assistant Examiner*—Alex Noguerola
*Attorney, Agent, or Firm*—Pillsbury Madison & Sutro LLP

[57] ABSTRACT

A heat exchanger is provided which may be used in an integrated blood oxygenator and heat exchanger. The heat exchanger has a plurality of wave shaped sinusoidal channels on one or both sides. The heat exchanger has a cap attached at the upper end. The heat exchanger is disposed within a housing. The bottom end of the heat exchanger is bonded to the bottom end of the housing, and the upper end of the heat exchanger with the cap attached is spaced apart from the upper end of the housing. A liquid inlet and outlet are in fluid communication with the inner surface of the heat exchanger. A blood inlet and outlet are in fluid communication with the outer surface of the heat exchanger. The heat exchanger may be used with a blood oxygenating chamber. The blood oxygenating chamber contains a plurality of permeable hollow fibers which oxygenate blood flowing through the blood oxygenating chamber. The blood oxygenating chamber is in fluid communication with the outer surface of the heat exchanger and the blood outlet.

35 Claims, 7 Drawing Sheets

INTEGRATED OXYGENATOR AND HEAT EXCHANGER

BACKGROUND OF THE INVENTION

The invention relates to an improved heat exchanger and an integrated blood heat exchanger and oxygenator and methods of making and using the same, and more specifically to a device which is compact and provides for improved oxygenation and heat exchange.

Various forms of blood oxygenators and heat exchangers are known in the prior art. Blood oxygenators and heat exchangers are commonly used during open heart surgery and are coupled to a cardiopulmonary bypass circuit to take over the function of the heart and lungs. The heat exchanger portion is typically used to cool the blood and lower the body temperature during open heart surgery. Reducing body temperature significantly reduces the demand for oxygen by various vital organs. Near the end of the surgery, the blood is heated to raise the body temperature.

During oxygenation, oxygen gas supplies oxygen to the blood and, in some oxygenators, releases $CO_2$. Two common types of oxygenators are bubble oxygenators and membrane oxygenators. With bubble oxygenators, gas bubbles containing oxygen are introduced directly into the blood. Usually, a defoamer is employed to remove gas bubbles from the blood following bubble oxygenation. Examples of bubble oxygenators are disclosed in U.S. Pat. Nos. 4,374,088 and 4,637,917. With membrane oxygenators, oxygen passes along one side of a permeable membrane and blood along the other. The permeable membrane has a sufficient pore size such that oxygen molecules pass through the membrane to be diffused into the blood as dissolved oxygen. However, the pores are sufficiently small such that blood cannot flow to the oxygen side. An example of the use of a microporous membrane sheet to oxygenate blood where blood flows along one side of a membrane sheet and oxygen along the other is disclosed in U.S. Pat. Nos. 4,451,562 and 4,424,190. Bundles of hollow fiber membrane tubes may also be used, where oxygen passes through the hollows of the tubes and blood flows along the outside of the tubes. Hollow tube membrane oxygenators are disclosed in U.S. Pat. Nos. 4,948,560, Re. 33,932, and 4,639,353.

SUMMARY OF THE DISCLOSURE

It is an object of preferred embodiments of the present invention to increase both the surface area along which heat exchange takes place and the duration of heat exchange. It is a further object to provide an increased surface area for both oxygenation and heat exchange within a compact housing. It is still a further object to provide a heat exchanger structure which reduces structural stress to the device.

These and other objects and advantages are achieved in an integrated heat exchanger and oxygenator wherein the heat exchanger is hollow and has an inner surface, an outer surface, a first end, and a second end. The heat exchanger is disposed within a housing having a first end and a second end. One of the inner surface and outer surface of the heat exchanger has a plurality of channels. A liquid inlet and liquid outlet are in fluid communication with the inner surface of the heat exchanger. A blood inlet and blood outlet are in fluid communication with the outer surface of the heat exchanger. A heat exchanger cap is attached to the second end of the heat exchanger. Preferably, the heat exchanger cap is brazed to the second end of the heat exchanger.

In preferred embodiments, the heat exchanger channels are longitudinal and wave-shaped (e.g., a sinusoidal wave shape), wherein the channels extend between the first and second ends of the heat exchanger. Preferably, the wave-shaped channels are on both the inner surface and outer surface of the heat exchanger. In preferred embodiments, the first end of the heat exchanger is fixed relative to the first end of the housing. The second end of the heat exchanger and heat exchanger cap may be spaced apart from the second end of the housing. In this way, the second end of the heat exchanger is not fixed relative to the second end of the housing, thereby significantly reducing the structural stress at the second end of the housing.

In preferred embodiments, a liquid baffle is disposed within the hollow heat exchanger. In such case, the liquid inlet and liquid outlet are in fluid communication with a space defined by the liquid baffle and inner surface of the heat exchanger. In one embodiment, the liquid baffle is hollow, wherein the liquid inlet and the hollow of the liquid baffle are in fluid communication with the inner surface of the heat exchanger.

The heat exchanger may be integrated with a blood oxygenator. In preferred embodiments of the integrated device, the outer surface of the heat exchanger and the blood outlet are in fluid communication with a blood oxygenating chamber. In preferred embodiments, a plurality of open hollow fibers, having a first end opening and a second end opening, extend through the blood oxygenating chamber. A gas inlet is in gas communication with a first gas manifold, wherein the first gas manifold is in communication with the first end opening of the hollow fibers. A first barrier, preferably comprised of urethane potting at the first end of the hollow fibers, prevents fluid communication between the first gas manifold and the blood oxygenating chamber. A gas outlet is in fluid communication with a second gas manifold, wherein the second gas manifold is in gas communication with the second end openings of the hollow fibers. A second barrier, preferably comprised of urethane potting at the second end of the hollow fibers, prevents fluid communication between the second gas manifold and the blood oxygenating chamber.

In preferred embodiments, the blood oxygenating chamber has an annular shape and surrounds the housing wall. The blood oxygenating chamber, housing, heat exchanger, and liquid baffle form a series of concentric shells, one within the other. Preferably, the integrated oxygenator and heat exchanger are in a vertical orientation, such that the first gas manifold, first barrier, heat exchanger second end, and housing second end are at the upper end of the device and the second gas manifold, second barrier, heat exchanger first end, and housing first end are at the lower end of the device.

A more detailed explanation of the invention is provided in the following description and claims, and is illustrated in the accompanying drawings.

DETAILED DESCRIPTION OF PREFERRED EMBODIMENTS

Figure 1:
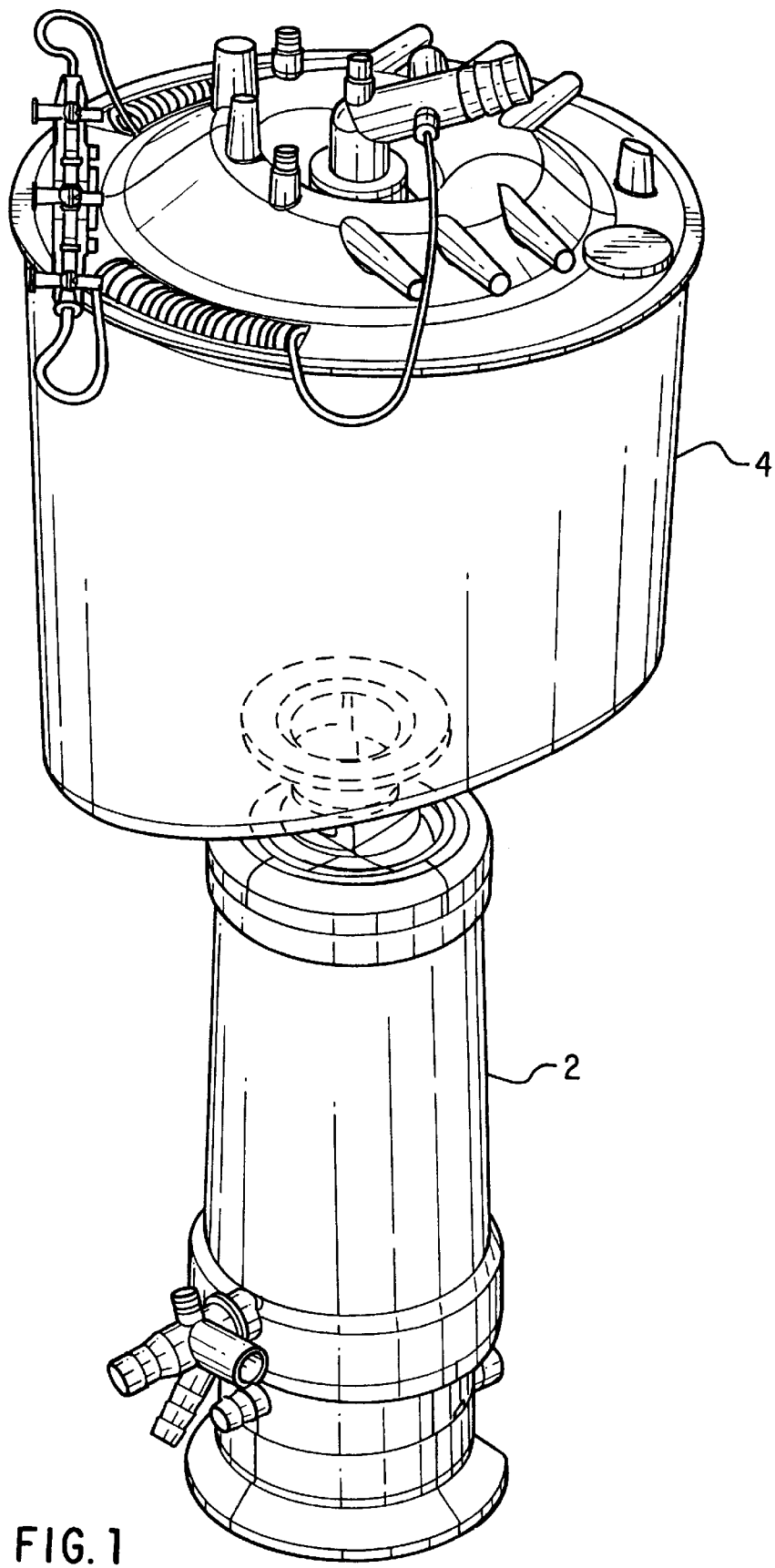
FIG. 1 shows an embodiment of an integrated oxygenator/heat exchanger 2 used in a system with a blood reservoir 4 which filters blood before it is transferred to the oxygenator/heat exchanger 2.

FIGS. 1–7 show preferred embodiments of an integrated oxygenator/heat exchanger 2. In the detailed description below, references made to the "top," "bottom," "upper," or "lower" portions of the oxygenator/heat exchanger 2, or elements thereof, are made with reference to the orientation of the structures shown in the drawings and are not intended to limit the scope of the invention where such limitations are not otherwise required.

As shown in FIG. 1, the oxygenator/heat exchanger 2 is preferably used in combination with a venous or combined venous and cardiotomy reservoir 4 which receives and stores a quantity of venous blood and filters the received blood. From the reservoir 4, the filtered blood is then transferred to the oxygenator/heat exchanger 2 via tubing (not shown). A pump, such as a peristaltic pump (not shown), may be applied to the tubing connecting the blood reservoir and oxygenator/heat exchanger. The pump is preferably controlled to provide the blood at a desired pressure to the oxygenator/heat exchanger 2.

Oxygenators and heat exchangers are often used in an extra-corporeal blood circuit during such surgical procedures as open heart surgery. During arterial incapacitation, the blood must be oxygenated. To this end, blood is transferred from the patient to oxygenation and heat exchange components. In the oxygenation component, oxygen is added to the blood and other gasses such as $CO_2$ are removed from the blood. In the heat exchange component, the blood is heated or cooled. After oxygenation and heat exchange are performed on the blood, the blood is returned to the patient.

Figure 2:
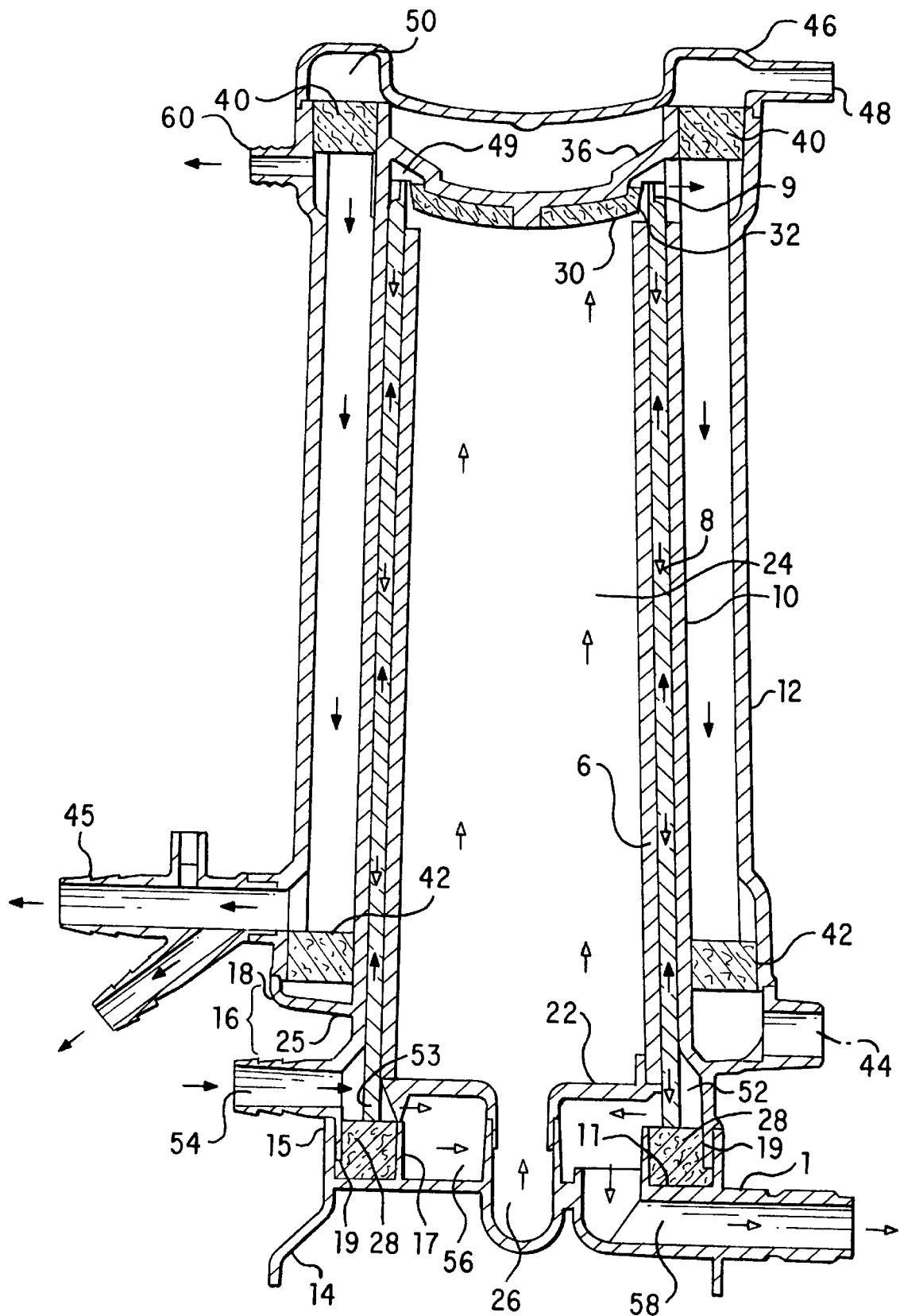
FIG. 2 provides a cross-sectional diagram of a preferred embodiment of the oxygenator/heat exchanger 2 of FIG. 1.
Figure 3:
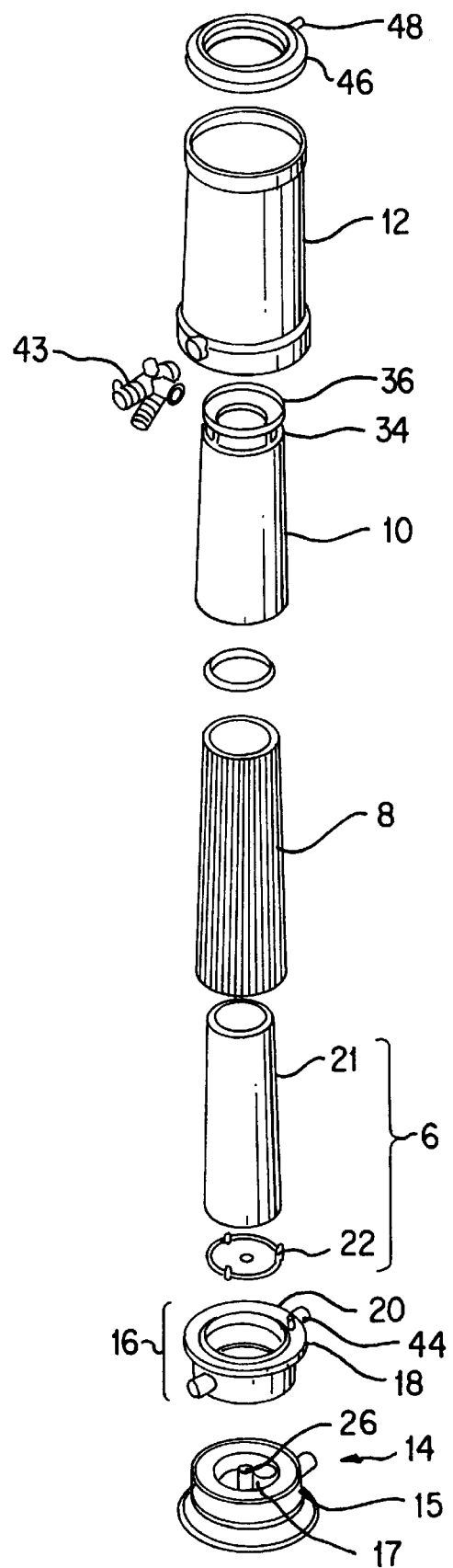
FIG. 3 provides an exploded layout of a preferred embodiment of the oxygenator/heat exchanger 2 of FIG. 1.

A preferred embodiment of the oxygenator/heat exchanger is described with reference to FIGS. 2, 3, 4, 5, 6, and 7. Referring to FIGS. 2 and 3, the oxygenator/heat exchanger 2, when assembled, can be characterized as comprising four concentric shells, each shell having a substantially cylindrical shape tapered toward the upper end. The innermost shell is a liquid baffle 6. The second shell is an annular heat exchanger 8 that is concentric with and surrounds the liquid baffle 6. The third annular shell is an inner housing wall 10 that is concentric with and surrounds the heat exchanger 8. The fourth annular shell is a cylindrical outer housing wall 12, also shown in FIG. 4, which is concentric with and surrounds the inner housing wall 10. A housing base 14 and lower manifold member 16 are disposed at the lower end (with reference to FIG. 2) of the four concentric shells. FIGS. 1-4 show preferred embodiments in a vertical orientation. It should be appreciated that preferred embodiments disclosed herein are not limited to being in a vertical orientation as shown in the Figures and can be positioned in numerous orientations, including a horizontal orientation.

FIG. 2 shows the four concentric shells coupled to the housing base 14 and lower manifold member 16. The heat exchange component is comprised of the liquid baffle 6, the heat exchanger 8, and the inner housing wall 10. Oxygenation occurs in the space between the inner housing wall 10 and outer housing wall 12.

FIGS. 2 and 3 show an embodiment of the housing base 14 having an annular outer wall 15, an annular inner wall 17, a liquid inlet tube 26, and a liquid outlet tube 58. FIGS. 2 and 3 also show the lower manifold member 16 having a lower annular wall 19 which branches upward into an annular outer wall 18 and an annular inner wall 20. In preferred embodiments, the housing base 14 and lower manifold member 16 are formed from separate components that are bonded together. The housing base outer wall 15 is bonded to the lower annular wall 19 of the lower manifold member 16. The bottom end of the inner housing shell 10 is bonded to the upper end of the inner wall 20 of the lower manifold member 16. The bottom end of the outer housing wall 12 is bonded to the upper end of the outer wall 18 of the lower manifold member 16.

In preferred embodiments, the outer housing wall 12, inner housing wall 10, the lower manifold member 16 (which includes the lower annular wall 19, outer wall 18, and the inner wall 20), and the housing base 14 (which includes the annular outer wall 15 and the annular inner wall 17) are separate polycarbonate components bonded together. It should be appreciated that in alternative embodiments, these components may be formed as one integral component or subcomponents bonded together. Still further materials other than polycarbonate may be used to form the housing elements.

In preferred embodiments as shown in FIGS. 2 and 3, the liquid baffle 6 is comprised of a hollow, generally cylindrical polycarbonate member having a generally cylindrical wall 21, a base 22, and an inner chamber 24 therein. FIG. 2 shows that the liquid baffle base 22 has a central opening for communication with a liquid inlet 26, which provides a liquid flow path to the inner chamber 24 of the liquid baffle 6. The base 22 is bonded to the bottom of the liquid baffle 6, and the base 22 in turn is bonded to the liquid inlet 26. In preferred embodiments, the liquid baffle 6 is tapered inward toward the top, such that the upper end of the baffle wall 21 defines a smaller diameter than the lower end of the wall 21. This is for ease of manufacture to facilitate the insertion of the heat exchanger 8 over the liquid baffle 6. It should be appreciated that in alternative embodiments the base 22 of the liquid baffle and liquid baffle wall 21 may be formed as a single integral unitary body instead of two components bonded together. Also, in further embodiments the liquid inlet 26 may be located other than through the center of the liquid baffle base 22.

The heat exchanger 8 is formed from a sheet of stainless steel which is pleated to form wave-like (e.g., sinusoidal) grooves on both sides of the steel sheet. These wave-like (e.g., sinusoidal) grooves cooperate with the inner surface of the inner housing wall 10 and the outer surface of the liquid baffle 6 to define wave-like (e.g., sinusoidal) liquid flow paths or channels, as described in more detail below. The definition of wave-like or wave-shaped is the common understanding of the word "wave" as defined in *Webster's Third New International Dictionary,* Merriam-Webster, Inc. Publishers (1986) which is "to follow a curving line or take a wavy form: undulate."

Figure 5A:
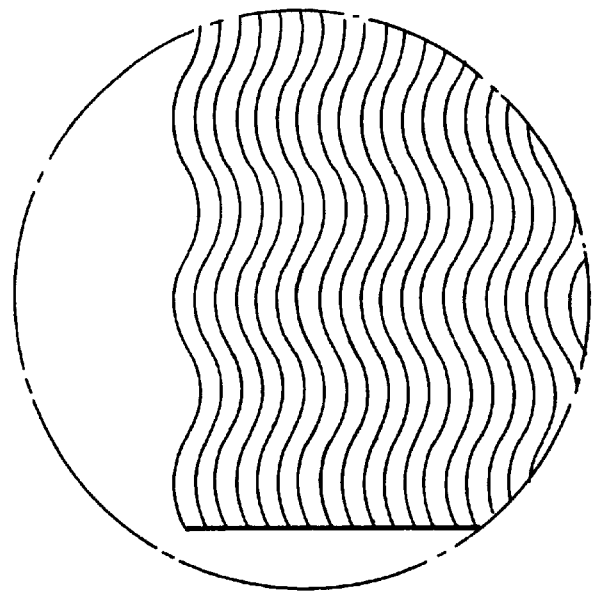
FIG. 5 shows the surface of heat exchanger material provided with sinusoidal grooves.
Figure 5B:
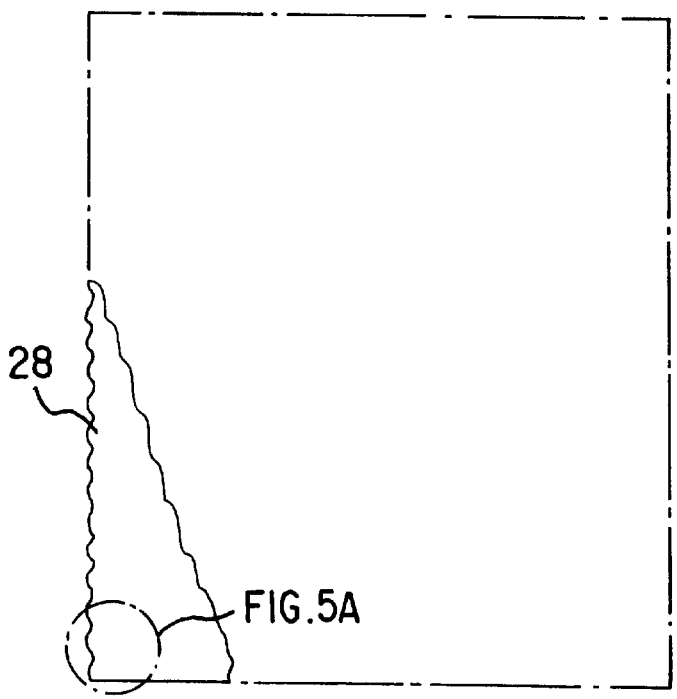
Figure 5C:
Figure 6:
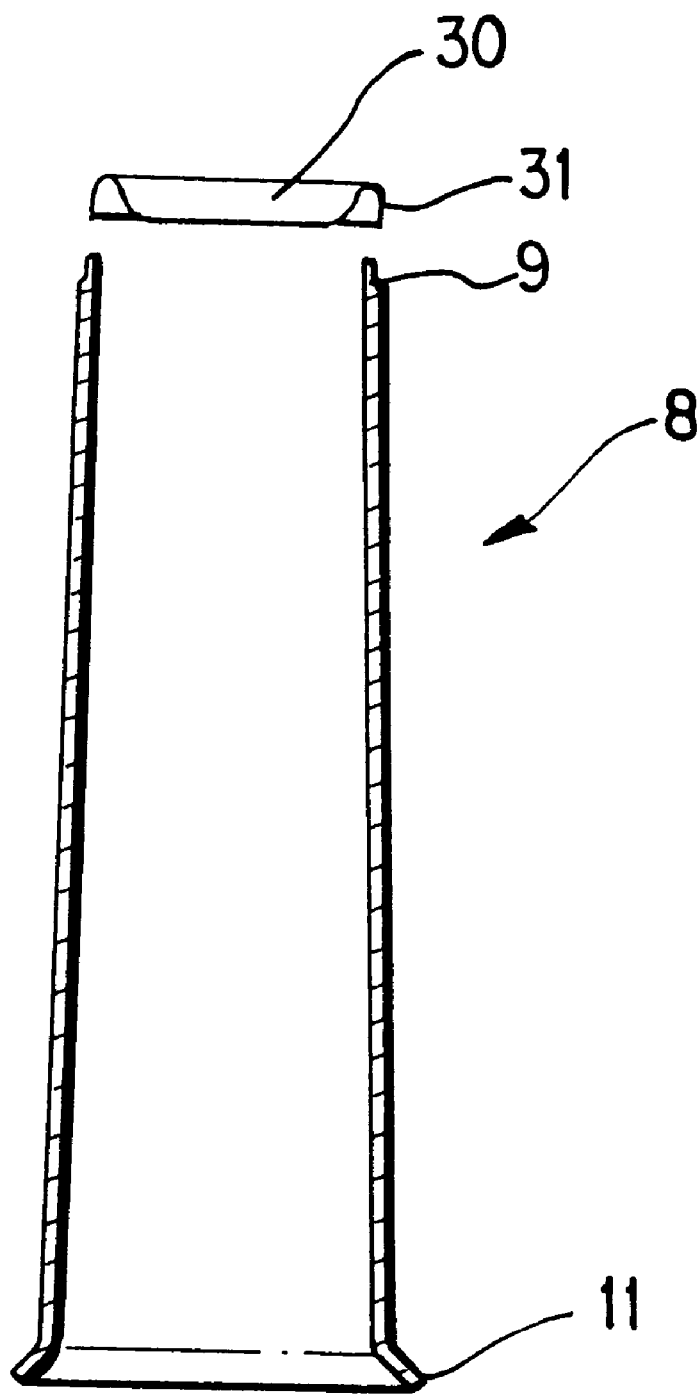
FIG. 6 shows a vertical cross-sectional perspective of a preferred embodiment of a heat exchanger.
Figure 7:
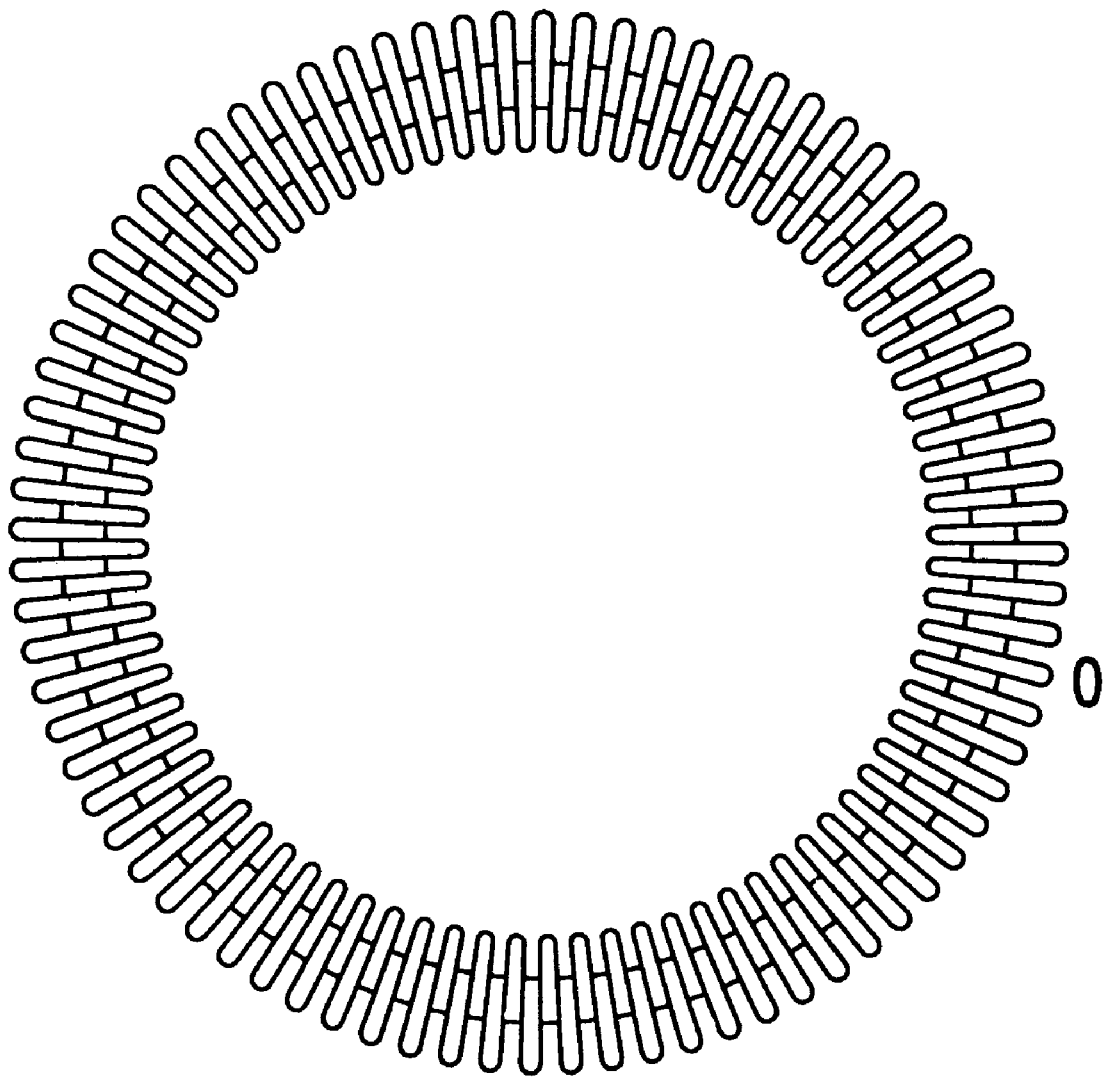
FIG. 7 shows a horizontal cross sectional perspective of the pleated sinusoidal surface of a heat exchanger.

Referring to FIG. 5, the wave-like (e.g., sinusoidal) grooves formed on both surfaces of the steel heat exchanger 8 sheet extend lengthwise, forming wave shaped channels that extend from the top to the bottom of the heat exchanger 8. The pleated sheet is then rolled to form a cylinder and laser welded along the ridge of the wave pattern. FIG. 7 provides a horizontal cross-section view of the channels formed on both surfaces of the heat exchanger 8. The heat exchanger is then tapered and the bottom end of the heat exchanger is flared outward 11 as shown in FIGS. 2 and 6. The top end 9 of the heat exchanger 8 is crimped as shown in FIG. 6.

As shown in FIG. 2, the bottom flared end 11 of the heat exchanger 8 is bonded in a urethane potting seal 28 which fills the annular space between the outer wall 15 and inner wall 17 of the housing base 14. The top crimped end 9 of the heat exchanger 8 is provided with a heat exchanger cap 30. Preferably, the heat exchanger cap 30 is made of stainless steel and is brazed to the top crimped end 9 of the heat exchanger 8. With reference to FIGS. 2 and 6, the heat exchanger cap 30 forms an annular indentation 31 around the circumference of the cap 30. The crimped top end 9 of the heat exchanger 8 is mated with the annular indentation 31 of the heat exchanger cap 30. The heat exchanger cap 30 is brazed to the crimped top end 9 of the heat exchanger 8. In this way, the heat exchanger cap 30 has surfaces brazed on both sides (i.e., the inner and outer sides) of the crimped top end 9 of the heat exchanger 8 to increase the bonding surface and hence the strength of the bond. In the preferred embodiment, the top of the heat exchanger cap 30 is filled with urethane potting 32 (FIG. 2). One advantage of this arrangement of the heat exchanger 8 in this embodiment is that the heat exchanger 8 is relatively rigid and need not be bonded at its upper end to the housing to hold its position. Instead, the upper end of the heat exchanger, in effect, "floats" relative to the upper end of the housing. By not bonding the upper end of the heat exchanger 8 to the housing, the risk of failure from stress at the upper part of the assembly is significantly reduced.

It should be appreciated that, in further embodiments, alternative structures for the heat exchanger 8 and heat exchanger cap 30 may be used and that the heat exchanger 8 may be coupled to the housing in various ways. In other embodiments, the cap 30 and heat exchanger 8 may be formed integral from a single piece of steel. Alternatively, material other than steel having suitable thermal conductivity could be used to form the heat exchanger 8 and cap 30. Further, the surfaces of the heat exchanger 8 may be pleated with grooves other than a sinusoidal shape, such as sawtooth, straight, or spiral shape, among others. Still further the heat exchanger 8 surfaces may be smooth and not pleated. In other alternative embodiments, structures such as ribs or guide rails may be attached to the surfaces of the heat exchanger 8 to form the channels which are formed by the pleated sinusoidal grooves in the illustrated preferred embodiment.

With reference to the assembled device shown in FIG. 2, the heat exchanger 8 includes upper 49 and lower 53 portions which extend beyond the top and bottom ends of the liquid baffle 6, respectively. A first set of liquid channels are formed in the space between the sinusoidal grooves on the inner surface of the heat exchanger 8 and the outer surface of the liquid baffle 6. A second set of liquid channels are formed in the space between the sinusoidal grooves on the outer surface of the heat exchanger 8 and the inner surface of the inner housing wall 10. The inner housing wall 10 extends from the inner wall 20 of the annular gas manifold 16, along the outside surface of the heat exchanger 8 to just below the upper end of the heat exchanger 8.

As shown in FIG. 3, in preferred embodiments, four struts 34 each having a top and bottom end extend from the top of the inner housing wall 10 beyond the upper end of the heat exchanger 8. Openings defined between the struts are provided for blood flow as described below. A concave inner housing cap 36 is attached at the top end of the struts 34. The concave inner housing cap 36 extends downward toward the heat exchanger cap 30. In preferred embodiments, the concave portion of the inner housing cap 36 extends downward to contact the urethane potting 32 filling the top of the heat exchanger cap 30. The inner housing cap 36 is positioned to contact the urethane potting 32 to minimize the collection of blood at the top of the heat exchanger cap 30.

In alternative embodiments, instead of forming apertures between struts extending from the inner housing wall 10, struts or openings of various shapes may be formed in the inner housing wall 10 to provide openings. Further, the inner housing cap 36, struts 34, and inner housing wall 10 may be formed from separate components bonded together or, alternatively, from a single unitary component, made of suitable material, such as, but not limited to polycarbonate.

With reference to FIG. 2, an annular oxygenating chamber 38 is formed in the space between the inner housing wall 10 and the outer housing wall 12. In preferred embodiments, a membrane formed of a bundle of microporous, hollow fiber membrane tubes, each having a top end and a bottom end, extend the length of the annular oxygenating chamber 38. Examples of a hollow fiber bundle used to oxygenate blood are disclosed in U.S. Pat. Nos. 4,948,560 and 4,659,549. In preferred embodiments, the hollow fiber bundle is comprised of polyporopylene hollow fibers woven into a mat. The fiber mat is held together with polyester threads spaced approximately 1 cm apart. Preferably two mats are used, one placed on top of the other with complementary skew angles. In a preferred embodiment, the width of a mat is approximately 204 mm. The wall thickness of each hollow tube is approximately 50 $\mu$m, the inner diameter is approximately 280 $\mu$m, the outer diameter is approximately 380 $\mu$m, and the maximum pore size is less than 0.2 $\mu$m. Additional embodiments may use different suitable dimensions for the fiber mat and the tubes, including different dimensions for the thickness, inner diameter, outer diameter, and pore size of the tube, and are not limited to the dimensions or arrangement of the mat and tubes disclosed herein.

The hollow fibers are potted at the top 40 and the bottom 42 ends. The hollow fibers have a sufficient pore size, less than 0.2 $\mu$m, to allow gas to flow through but have a sufficiently small diameter to prevent liquid from flowing through the pores. Thus, the fibers are pervious to gas, but impervious to liquid, such that oxygen and $CO_2$ may transfer through the fiber walls, but blood may not. In further embodiments, other suitable types of oxygen transferring means may be provided in the annular oxygenating chamber 38, including, but not limited to, sheet type membranes, pleated membranes, and bubble oxygenators. However, with reference to the illustrated fiber membrane embodiment, the annular oxygenating chamber 38 is defined at its top and bottom by the potted top 40 and bottom 42 ends of the hollow fibers. A blood outlet 45, also shown in FIG. 4, is located near the bottom of the annular oxygenating chamber 38.

In preferred embodiments, the inside surface of the upper and lower ends of the outer housing wall 12 and the outside surface of the upper and lower ends of the inner housing wall 10 each have a plurality of grooves where the hollow fibers are potted 40, 42. These grooves provide additional surface area for the potting 40, 42, thereby increasing the strength of the bond, and function as a barrier to the propagation of delamination.

Figure 4:
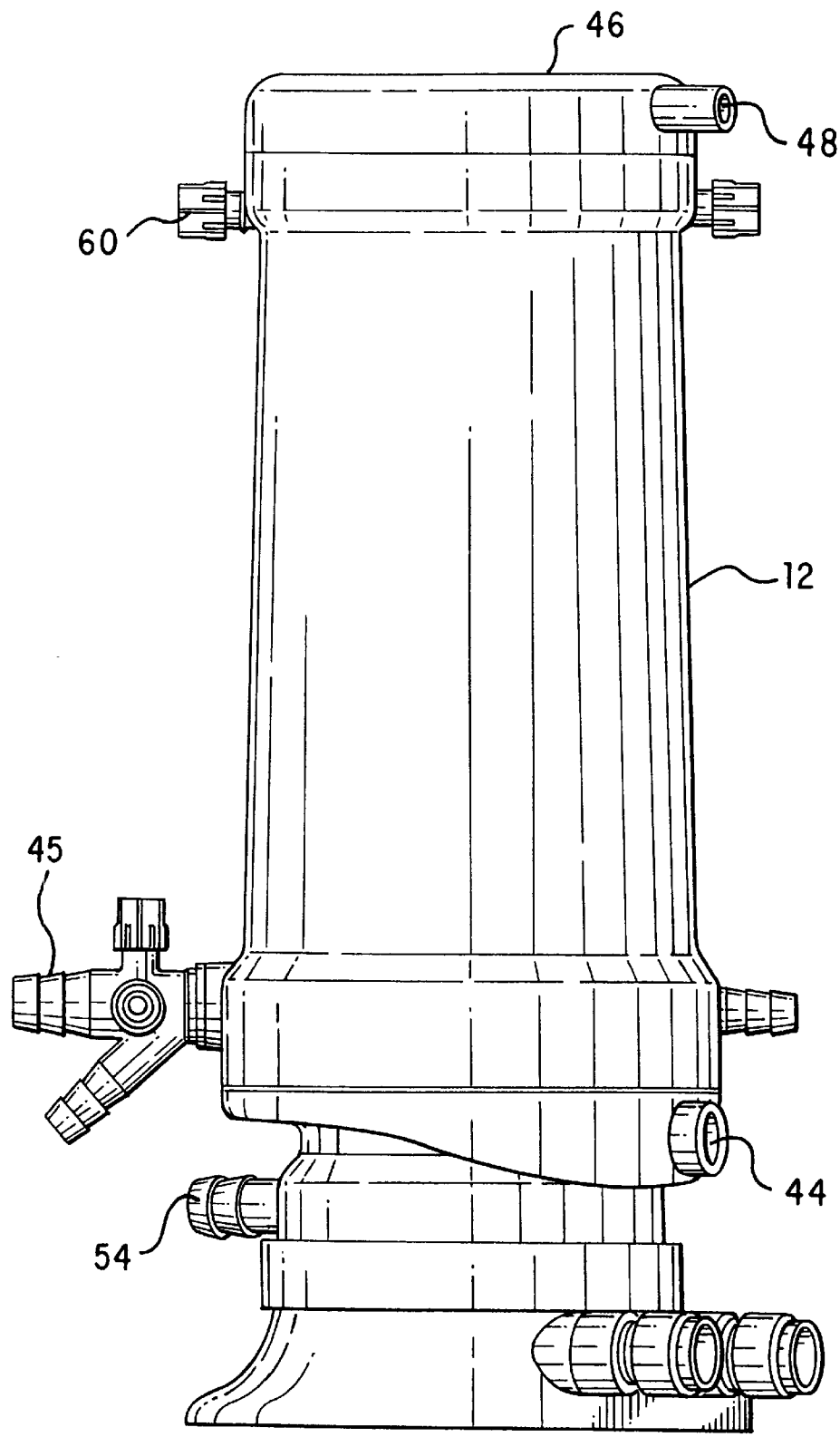
FIG. 4 provides an external view of the preferred embodiment of the oxygenator/heat exchanger 2 of FIG. 1.

With reference to FIGS. 2, 3, and 4, a housing cap 46 is bonded to the upper end of the outer housing wall 12. The housing cap 46 has a gas inlet 48. An upper annular gas manifold 50 is formed in the space between the housing cap 46 and the potted top end of the bundle of fibers 40. The hollow interior of the fibers is in gas flow communication with the upper annular gas manifold 50 and the gas inlet 48. A lower annular gas manifold 43 is formed in the space between the annular outer wall 18 and the annular inner wall 20 of the lower manifold member 16 and the potted bottom end of the fibers 42. A gas outlet 44 (FIGS. 2 and 4) is provided in the lower manifold member 16 and opens into the lower gas manifold 43. The hollow interior of the fibers is in gas flow communication with the lower annular gas manifold 43 and the gas outlet 44.

As shown in FIG. 2, an annular blood entrance manifold 52 is formed in the area between the lower annular wall 19 of the lower manifold member 16, the heat exchanger 8 and the portion of the urethane potting 28 extending between the outer surface of the heat exchanger 8 and the outer wall 15 of the housing base 14. A blood inlet 54 (FIG. 4) is provided in the lower manifold member 16 and opens into the blood entrance manifold 52. As shown in FIG. 2, a lower liquid chamber 56 is formed by the liquid baffle base 22, the inner surface of the lower portion 53 of the heat exchanger 8, the housing base 14, and the portion of the urethane potting 28 extending between the inside surface of the heat exchanger 8 and the inner wall 17 of the housing base 14. A liquid outlet 58 provided in the housing base 14 opens into the lower liquid chamber 56.

The preferred embodiment shown in FIGS. 2 and 4 also includes a gas vent 60 provided near the upper end of the outer housing wall 12. The gas vent 60 is in gas communication with the upper part of the annular oxygenating chamber 38 to vent gas from the blood flowing through the annular oxygenating chamber 38. Other or additional gas vents may also be provided to allow gas to escape from the blood.

In operation, with reference to the preferred embodiment of FIG. 2, water (or other suitable fluid) is supplied from an external source (or recirculated from the outlet 58) to the liquid inlet 26 at sufficient pressure to allow the water (or other fluid) to flow upward and substantially fill the inner chamber 24 of the liquid baffle 6. Water then flows over the top end of the liquid baffle 6 and flows downward through serpentine liquid channels formed by the sinusoidal grooves on the inside surface of the heat exchanger 8 and the outer surface of the liquid baffle 10. Water flows downward into the lower liquid chamber 56 and then exits the oxygenator/heat exchanger through the liquid outlet 58.

A mixture of oxygen gas is provided to the device at the gas inlet 48 (FIGS. 2 and 4). The oxygen gas flows into the upper annular gas manifold 50 and then through the hollow of the fibers. Oxygen may pass laterally through the fiber pores and be absorbed by the blood flowing outside of the fibers in the annular oxygenating chamber 38. Similarly, gas molecules from the blood, such as $CO_2$, may be released from the blood and pass into the hollow interior of the fibers and then flow downward through the end of the potted fibers 42 into the lower annular gas manifold 43. From there, the gas flows out the gas outlet 44. As noted above, gas in the blood may also exit the annular fiber chamber 30 through vent 60.

As water and oxygen gas are flowing through the device through separate flow paths, blood is provided to the blood inlet 54. The blood may be transferred to the inlet 54 from a reservoir, such as blood reservoir 4 (FIG. 1), or directly from a patient. Preferably, the blood is provided at a pressure sufficient to allow the blood to flow into the annular blood entrance manifold 52. From the blood entrance manifold 52, blood flows upward through the serpentine channels formed by the sinusoidal grooves on the outer surface of the heat exchanger 8 and the inner surface of the inner housing wall 10. While blood is flowing along the outer surface of the heat exchanger 8, heat is transferred between the blood and the fluid flowing on opposite sides of the heat exchanger 8, through the heat exchanger 8 material. If the blood is to be warmed, then the fluid flowing opposite the blood along the heat exchanger 8 is provided at a higher temperature than the blood. If the blood is to be cooled, the fluid is provided at a lower temperature.

The blood flows to the top of the inner housing wall 10 and then passes through the openings formed by the struts 34 (FIG. 3) down into the annular oxygenating chamber 38. Blood flows downward through the annular oxygenating chamber 38 along the outer surface of the fibers. The blood is oxygenated as it flows along the fibers. When reaching the bottom of the annular oxygenating chamber 38, the blood flows out the blood outlet 45 and may be transferred to the patient.

As described in detail above, preferred embodiments of the present invention provide a compact housing integrating both the oxygenation and heat exchange components in a single unit. Preferred embodiments maximize the surface along which heat exchange takes place while maintaining a gentle blood flow path by utilizing wave-shaped blood channels. Maximizing the surface along which heat exchange takes place additionally maximizes the duration of the heat exchange process (time during which blood passes along the heat exchange surface) in order to insure that the blood is cooled or warmed to the desired temperature of the fluid. Preferred embodiments further maximize the surface along which oxygenation takes place by using a plurality of hollow fiber tubes. It should be appreciated that alternative structures for providing a compact, integrated oxygenator/heat exchanger could be used, including those alternatives discussed above. As such, the scope of the integrated oxygenator/heat exchanger invention should not be limited to the specific embodiments disclosed and illustrated herein, but should be defined only by the appended claims and equivalents thereof.

We claim:

1. A blood heat exchanger apparatus comprising:
   (a) a hollow housing having a first end and a second end;
   (b) a hollow, cylindrical heat exchanger having an inner surface, an outer surface, a first end, and a second end, wherein the inner surface and outer surface are both generally cylindrical and elongated, further wherein both the inner surface and outer surface have a plurality of in-phase, elongated wave-shaped channels defining a plurality of wave-shaped liquid flow paths extending from the first end of the heat exchanger to the second end thereof, wherein the heat exchanger is disposed within the hollow housing and the first end of the heat exchanger is fixed relative to the housing;
   (c) a heat exchanger cap coupled to the second end of the heat exchanger, wherein the heat exchanger cap and the second end of the heat exchanger are spaced apart from the second end of the housing;
   (d) a liquid inlet in fluid communication with the inner surface of the heat exchanger;
   (e) a liquid outlet in fluid communication with the inner surface of the heat exchanger;
   (f) a blood inlet in fluid communication with the outside surface of the heat exchanger; and
   (g) a blood outlet in fluid communication with the outside surface of the heat exchanger.

2. The heat exchanger apparatus of claim 1, wherein the housing and heat exchanger are in a vertical orientation, the vertical orientation having an upper and a lower end, wherein the housing and heat exchanger first end are at the lower end and the housing and heat exchanger second end are at the upper end.

3. The heat exchanger of claim 1, wherein the heat exchanger is formed by welding two sides of a substantially flat heat exchanger together to form a substantially cylindrical heat exchanger, further wherein the plurality of in-phase wave-shaped channels are formed by pleating the substantially flat heat exchanger.

4. The heat exchanger of claim 1, wherein the channels are longitudinal, wave-shaped channels that extend between the first end and second end of the heat exchanger.

5. The heat exchanger of claim 4, wherein the longitudinal, wave-shaped channels have a sinusoidal wave shape.

6. The heat exchanger of claim 1, wherein a liquid baffle is disposed within the hollow of the heat exchanger and spaced apart from the inner surface of the heat exchanger, and wherein the liquid inlet and liquid outlet are in fluid communication with a space defined by the liquid baffle and the inner surface of the heat exchanger.

7. The heat exchanger of claim 6, wherein the liquid baffle is hollow, wherein the liquid inlet opens into the hollow of the liquid baffle, wherein the hollow of the liquid baffle and the liquid outlet are in fluid communication with the space defined by the liquid baffle and the inner surface of the heat exchanger.

8. An integrated oxygenator and heat exchanger apparatus, comprising:
(a) a heat exchanger component, comprising:
  i. a hollow housing having a first end and a second end;
  ii. a hollow, cylindrical heat exchanger having an inner surface, an outer surface, a first end, and a second end, wherein the inner surface and outer surface are both generally cylindrical and elongated, further wherein both the inner surface and outer surface have a plurality of in-phase, elongated wave-shaped channels defining a plurality of wave-shaped liquid flow paths, wherein the first end of the heat exchanger is fixed relative to the housing, and wherein the heat exchanger is disposed within the hollow housing;
  iii. a heat exchanger cap coupled to the second end of the heat exchanger, wherein the heat exchanger cap and second end of the heat exchanger are spaced apart from the second end of the housing;
  iv. a liquid inlet in fluid communication with the inner surface of the heat exchanger;
  v. a liquid outlet in fluid communication with the inner surface of the heat exchanger;
  vi. a blood inlet in fluid communication with the outside surface of the heat exchanger; and
  vii. a blood outlet in fluid communication with the outside surface of the heat exchanger; and
(b) a blood oxygenating chamber in fluid communication with the outside surface of the heat exchanger, wherein the blood outlet is in fluid communication with the blood oxygenating chamber.

9. The integrated oxygenator and heat exchanger apparatus of claim 8, wherein the plurality of channels are longitudinal wave-shaped channels extending between the first end and second end of the heat exchanger.

10. The integrated oxygenator and heat exchanger apparatus of claim 8, further comprising:

(a) a plurality of hollow fibers having a first end, a second end, and openings at each end, wherein the hollow fibers extend through the blood oxygenating chamber;
(b) an oxygen gas inlet;
(c) an oxygen gas outlet;
(d) a first gas manifold in gas communication with the first end openings of the hollow fibers and the oxygen gas inlet;
(e) a first barrier preventing fluid communication between the blood oxygenating chamber and the first gas manifold and the first end openings of the hollow fibers;
(f) a second gas manifold in gas communication with the second end openings of the hollow fibers and the oxygen gas outlet; and
(g) a second barrier preventing fluid communication between the blood oxygenating chamber and the second gas manifold and the second end openings of the hollow fibers.

11. The integrated oxygenator and heat exchanger of claim 10, wherein the blood oxygenating chamber is annular and surrounds the housing, and wherein the hollow housing, hollow heat exchanger, and blood oxygenating chamber form a series of concentric shells.

12. The integrated oxygenator and heat exchanger of claim 10, wherein the first barrier is formed of urethane potting at the first end of the hollow fibers and wherein the second barrier is formed of urethane potting at the second end of the hollow fibers.

13. The integrated oxygenator and heat exchanger of claim 10, wherein a liquid baffle is disposed within the hollow of the heat exchanger and spaced apart from the inner surface of the heat exchanger, and wherein the liquid inlet and liquid outlet are in fluid communication with a space defined by the liquid baffle and the inner surface of the heat exchanger.

14. The integrated oxygenator and heat exchanger of claim 13, wherein the liquid baffle is hollow, wherein the liquid inlet opens into the hollow of the liquid baffle, wherein the hollow of the liquid baffle and the liquid outlet are in fluid communication with the space defined by the liquid baffle and the inner surface of the heat exchanger.

15. The integrated oxygenator and heat exchanger of claim 10, wherein the integrated oxygenator and heat exchanger is in a vertical orientation, and the first gas manifold, housing second end, and heat exchanger second end are at the upper end of the vertical orientation, and wherein the second gas manifold, housing first end, and heat exchanger first end are at the lower end of the vertical orientation.

16. The integrated oxygenator and heat exchanger apparatus of claim 8, wherein the wave-shaped channels are longitudinal and have a sinusoidal wave shape.

17. A blood heat exchanger apparatus, comprising:
(a) a hollow housing having a first end and a second end;
(b) a hollow, cylindrical heat exchanger having an inner surface, an outer surface, a first end, and a second end, wherein the inner surface and outer surface are both generally cylindrical and elongated, further wherein both of the inner surface and outer surface have a plurality of in-phase, elongated wave-shaped channels defining a plurality of wave-shaped liquid flow paths, wherein the heat exchanger is disposed within the hollow housing and fixed relative thereto;
(c) a liquid inlet in fluid communication with the inner surface of the heat exchanger;
(d) a liquid outlet in fluid communication with the inner surface of the heat exchanger;

(e) a blood inlet in fluid communication with the outside surface of the heat exchanger; and (f) a blood outlet in fluid communication with the outside surface of the heat exchanger.

18. The heat exchanger apparatus of claim 17, wherein the wave-shaped channels are longitudinal and have a sinusoidal wave shape.

19. The heat exchanger apparatus of claim 17, wherein the housing and heat exchanger are in a vertical orientation, the vertical orientation having an upper and a lower end, wherein the housing and heat exchanger first end are at the lower end and the housing and heat exchanger second end are at the upper end.

20. The heat exchanger of claim 17, wherein the wave-shaped channels are longitudinal and extend between the first end and the second end of the heat exchanger.

21. The heat exchanger of claim 17, wherein both the inner surface and outer surface of the heat exchanger both have wave-shaped channels extending between the first end and second end of the heat exchanger.

22. The heat exchanger of claim 17, wherein a liquid baffle is disposed within the hollow of the heat exchanger and spaced apart from the inner surface of the heat exchanger, and wherein the liquid inlet and liquid outlet are in fluid communication with a space defined by the liquid baffle and the inner surface of the heat exchanger.

23. The heat exchanger of claim 22, wherein the liquid baffle is hollow, wherein the liquid inlet opens into the hollow of the liquid baffle, wherein the hollow of the liquid baffle and the liquid outlet are in fluid communication with the space defined by the liquid baffle and the inner surface of the heat exchanger.

24. An integrated oxygenator and heat exchanger apparatus, comprising:

(a) a heat exchanger component, comprising:
   i. a hollow housing having a first end and a second end;
   ii. a hollow, cylindrical heat exchanger having an inner surface, an outer surface, a first end, and a second end, wherein the inner surface and outer surface are both generally cylindrical and elongated, further wherein both of the inner surface and outer surface have a plurality of in-phase, elongated wave-shaped channels defining a plurality of wave-shaped liquid flow paths, wherein the heat exchanger is disposed within the hollow housing and fixed relative thereto;
   iii. a liquid inlet in fluid communication with the inner surface of the heat exchanger;
   iv. a liquid outlet in fluid communication with the inner surface of the heat exchanger;
   v. a blood inlet in fluid communication with the outside surface of the heat exchanger; and
   vi. a blood outlet in fluid communication with the outside surface of the heat exchanger; and (b) a blood oxygenating chamber including a blood oxygenating means in fluid communication with the outside surface of the heat exchanger, wherein the blood outlet is in fluid communication with the blood oxygenating chamber.

25. The integrated oxygenator and heat exchanger apparatus of claim 24 wherein the wave-shaped channels are longitudinal and extend between the first end and the second end of the heat exchanger.

26. The integrated oxygenator and heat exchanger of claim 24, wherein both the inner surface and outer surface of the heat exchanger have a plurality of wave-shaped channels.

27. The integrated oxygenator and heat exchanger of claim 24, further comprising:

(a) a plurality of hollow fibers having a first end, a second end, and openings at each end, wherein the hollow fibers extend through the blood oxygenating chamber;

(b) an oxygen gas inlet;

(c) an oxygen gas outlet;

(d) a first gas manifold in gas communication with the first end openings of the hollow fibers and the oxygen gas inlet;

(e) a first barrier preventing fluid communication between the blood oxygenating chamber and the first gas manifold and the first end openings of the hollow fibers;

(f) a second gas manifold in gas communication with the second end openings of the hollow fibers and the oxygen gas outlet;

(g) a second barrier preventing fluid communication between the blood oxygenating chamber and the second gas manifold and the second end openings of the hollow fibers.

28. The integrated oxygenator and heat exchanger of claim 27, wherein the hollow housing, hollow heat exchanger, and blood oxygenating chamber form a series of concentric shells, and wherein the blood oxygenating chamber is annular and surrounds the housing.

29. The heat exchanger of claim 27, wherein the blood oxygenating chamber, housing, and heat exchanger are in a vertical orientation, wherein the second gas manifold, second barrier, heat exchanger first end, and housing first end are at the lower end of the vertical orientation and the first gas manifold, first barrier, housing second end, and heat exchanger second end are at the upper end of the vertical orientation.

30. The integrated heat exchanger and oxygenator of claim 27, wherein the first barrier is formed of urethane potting at the first end of the hollow fibers and wherein the second barrier is formed of urethane potting at the second end of the hollow fibers.

31. The integrated heat exchanger and oxygenator of claim 27, wherein a liquid baffle is disposed within the hollow of the heat exchanger and spaced apart from the inner surface of the heat exchanger, and wherein the liquid inlet and liquid outlet are in fluid communication with a space defined by the liquid baffle and the inner surface of the heat exchanger.

32. The heat exchanger of claim 31, wherein the liquid baffle is hollow, wherein the liquid inlet opens into the hollow of the liquid baffle, wherein the hollow of the liquid baffle and the liquid outlet are in fluid communication with the space defined by the liquid baffle and the inner surface of the heat exchanger.

33. The integrated oxygenator and heat exchanger apparatus of claim 24, wherein the wave-shaped channels are longitudinal and have a sinusoidal wave shape.

34. A blood heat exchanger apparatus comprising:

(a) a hollow housing having an inner surface, an outer surface, first end and a second end, wherein the inner surface of the hollow housing is generally smooth;

(b) a hollow, cylindrical heat exchanger having an inner surface, an outer surface, a first end and a second end, wherein the inner surface and outer surface are both generally cylindrical and elongated, further wherein both the inner surface and outer surface have a wave-shaped surface defining wave-shaped liquid flow paths extending from the first end of the heat exchanger to the second end thereof, wherein the heat exchanger is disposed within the hollow housing and the first end of the heat exchanger is fixed relative to the housing;

(c) a liquid inlet in fluid communication with the inner surface of the heat exchanger;
(d) a liquid outlet in fluid communication with the inner surface of the heat exchanger;
(e) a blood inlet in fluid communication with the outside surface of the heat exchanger; and
(f) a blood outlet in fluid communication with the outside surface of the heat exchanger, and wherein blood flows between and along the smooth inner surface of the housing and the wave-shaped liquid flow path on the outer surface of the heat exchanger.

35. The heat exchanger apparatus of claim 34, wherein the wave-shaped surface defining wave-shaped flow paths are formed by pleating the surface of the heat exchanger.

* * * * *